(12) United States Patent
Itescu et al.

(10) Patent No.: US 9,415,072 B2
(45) Date of Patent: Aug. 16, 2016

(54) EXPANSION OF HAEMOPOIETIC PRECURSORS

(71) Applicants: Silviu Itescu, Melbourne (AU); Michael David Schuster, New York, NY (US)

(72) Inventors: Silviu Itescu, Melbourne (AU); Michael David Schuster, New York, NY (US)

(73) Assignee: MESOBLAST, INC., New York, NY (US)

(*) Notice: Subject to any disclaimer, the term of this patent is extended or adjusted under 35 U.S.C. 154(b) by 0 days.

(21) Appl. No.: 14/476,467

(22) Filed: Sep. 3, 2014

(65) Prior Publication Data

US 2015/0202232 A1 Jul. 23, 2015

Related U.S. Application Data

(63) Continuation of application No. 13/061,693, filed as application No. PCT/AU2009/001145 on Sep. 3, 2009, now Pat. No. 8,828,375.

(60) Provisional application No. 61/190,967, filed on Sep. 3, 2008.

(51) Int. Cl.
| | |
|---|---|
| *H04B 15/00* | (2006.01) |
| *H04L 5/00* | (2006.01) |
| *H04W 24/02* | (2009.01) |
| *A61K 35/28* | (2015.01) |
| *C12N 5/0789* | (2010.01) |
| *A61K 45/06* | (2006.01) |
| *A61K 35/12* | (2015.01) |

(52) U.S. Cl.
CPC .............. *A61K 35/28* (2013.01); *A61K 45/06* (2013.01); *C12N 5/0647* (2013.01); *A61K 2035/124* (2013.01); *C12N 2501/125* (2013.01); *C12N 2501/145* (2013.01); *C12N 2501/22* (2013.01); *C12N 2501/26* (2013.01); *C12N 2502/1352* (2013.01); *C12N 2502/1358* (2013.01)

(58) Field of Classification Search
CPC .............................. A61K 35/28; C12N 5/0647
See application file for complete search history.

(56) References Cited

U.S. PATENT DOCUMENTS 8,828,375 B2 * 9/2014 Itescu et al. .................. 424/85.2

OTHER PUBLICATIONS

Gonçalves et al (Experimental Hematology. 2006; 34: 1353-1359).*
Gronthos et al. (J. Cell Science. 2003; 116: 1827-1835).*
Weisdorf et al. (Blood. 1995; 85: 3452-3456).*

* cited by examiner

*Primary Examiner* — Scott Long
(74) *Attorney, Agent, or Firm* — John P. White; Cooper & Dunham LLP (57) ABSTRACT

The present invention relates to a method of transplanting haematopoietic precursor cells into a subject in need thereof which involves culturing the haematopoietic precursor cells in the presence of a population of cells enriched for STRO-$1^{bright}$ cells. The method of the present invention is useful in the treatment of haematological disorders.

19 Claims, 1 Drawing Sheet

EXPANSION OF HAEMOPOIETIC PRECURSORS

FIELD OF THE INVENTION

The present invention relates the present invention relates to a method of transplanting haematopoietic precursor cells into a subject in need thereof which involves culturing the haematopoietic precursor cells in the presence of a population of cells enriched for STRO-1$^{bright}$ cells. The method of the present invention is useful in the treatment of haematological disorders.

BACKGROUND OF THE INVENTION

For more than a decade, umbilical cord blood (CB) has been investigated clinically as an alternative source of hematopoietic progenitors for allogeneic transplantation of patients lacking an HLA-matched marrow donor. Fewer T-cells and/or less developed T-cells in CB compared to marrow allows for the possibility that CB grafts will produce less Graft vs. Host Disease (GVHD), the major cause of morbidity and mortality in the allogeneic transplant setting. Other potential advantages include the ability to markedly increase the number of allografts available and thus the number of patients who could be transplanted, given the availability and ease of collecting CB from placental veins prior to disposal of the placenta, compared to collecting bone marrow or peripheral blood progenitor cells (PBPCs) from living donors. This new source of hematopoietic progenitors has allowed CB banks to target collection of units with human leukocyte antigen (HLA) types such as those of minority African American and Hispanic populations, which are under-represented in the National Marrow Donor Program Registry.

Since the first CB transplant performed in 1988, more than 5,000 patients world-wide have received related or unrelated CB transplants for a variety of malignant and non-malignant diseases. The majority of CB recipients have been children although adults are increasingly receiving CB transplants when an HLA– matched donor is not available. The progression-free survival rates reported thus far are comparable to results achieved following allogeneic bone marrow transplantation (Barker J N et al., (2001)). Moreover, there are many reports of what appears to be less GVHD than that associated with bone marrow transplants, despite the use of CB grafts with substantially more donor-recipient HLA disparity than that tolerated in recipients of marrow or PBPC allografts. The major disadvantage of CB is the low cell dose, which results in slower time to engraftment and higher rates of engraftment failure when compared to bone marrow transplantation (Kernan N A et al. (1993)). In studies of CB transplantation published by Kurtzberg (Kurtzberg J., (1996)), Gluckman (Gluckman et al., (1997)), Rubinstein (Rubinstein P., (1998)), Rizzieri (Rizzieri D A et al., (2001)), and Laughlin (Laughlin M J et al., (2001)) the median times to an absolute neutrophil count (ANC) of $\geq 0.5 \times 10^9$/L ranged from 22 to 34 days. Median times to a transfusion-independent platelet count $\geq 20 \times 10^9$/L varied from 56 to over 100 days, with engraftment failure rates of 12-18%. However, the engraftment failure rate for the adult patients (>18 years old and/or >45 Kg) in those series was substantially higher, ranging from 10-62%. It is these larger, adult patients, who might benefit the most from the ex vivo expansion of CB progenitor cells.

From the studies referenced above, there appears to be a threshold effect in the total nucleated cell (TNC) dose of unmanipulated CB infused and time to engraftment. In Gluckman's study, engraftment and survival were superior in patients who received $\geq 3.7 \times 10^7$ TNC/Kg. This large a cell dose is not generally available for patients weighing more than 45 kg. For adult patients, it appears that recipients of $\geq 1.0 \times 10^7$ TNC/Kg had more favorable engraftment than recipients of lower cell doses. Kurtzberg et al., reported a linear correlation between the number of CB nucleated cells infused and time to neutrophil engraftment (p<0.002) in the unrelated CB transplant setting. These data suggest that giving more CB cells may result in faster neutrophil engraftment.

SUMMARY OF THE INVENTION

The present inventors have developed a method for expanding haemopoietic progenitor cells (HPCs) by co-culturing with a population of cells enriched for STRO-1$^{bright}$ cells or progeny thereof. The expanded HPCs can be used for transplantation into a subject in need thereof, such an individual with a haematological disorder.

Accordingly, the present invention provides a method of transplanting haematopoietic precursor cells into a subject in need thereof, the method comprising:
   culturing haematopoietic precursor cells in the presence of a population of cells enriched for STRO-1$^{bright}$ cells or supernatant or progeny derived therefrom, wherein such STRO-1$^{bright}$ cells are mesenchymal precursor cells (MPC) which comprise mesenchymal precursor cells capable of giving rise to colony forming unit-fibroblasts (CFU-F), so as to expand the haematopoietic precursor cells; and
   administering the expanded haematopoietic precursor cells to a subject.

In one embodiment of the invention the population of cells enriched for STRO-1$^{bright}$ cells are allogeneic cells.

In another embodiment, the STRO-1$^{bright}$ enriched cells are grown to >70% confluency for cord blood co-culture by about four days after initiating culture.

In another embodiment, the ratio of STRO-1$^{bright}$ enriched cells to hematopoietic precursor cells at the start of the co-culture is about 1:4, about 1:5, about 1:6, about 1:7, about 1:8, about 1:9 or about 1:10.

The STRO-1$^{bright}$ enriched cells may be derived from any suitable tissue source. Examples of suitable tissue sources include bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis and periosteum.

In another embodiment, the haematopoietic precursor cells are derived from cord blood. The haematopoietic precursor cells may or may not be isolated from the cord blood prior to expansion. Thus, in one embodiment the method comprises co-culturing unmanipulated cord blood cells with the population of cells enriched for STRO-1$^{bright}$ cells or progeny thereof.

In another embodiment of the invention the expanded haematopoietic precursor cells comprise CFU-GM cells. The expanded haematopoietic precursor cells may comprise at least $1 \times 10^4$ CFU-GM cells per kg of subject body weight.

In another embodiment of the invention, haematopoietic reconstitution occurs in the subject following administration of the expanded haematopoietic precursor cells. For example, haematopoietic reconstitution may occur in the subject within 30 days, more preferably within 25 days, more preferably within 20 days, more preferably within 15 day and more preferably within 10 days of administration of the expanded haematopoietic precursor cells.

In yet another embodiment, haematopoietic reconstitution occurs in the absence of an adverse immune response. In this embodiment, administration of the expanded haematopoietic precursor cells does not result in significant graft rejection.

Haematopoietic reconstitution may determined by any one of a number of suitable measurements. For example, haematopoietic reconstitution may be determined by neutrophil engraftment, platelet engraftment, lymphoid engraftment, erythroid engraftment and/or megakaryocyte engraftment.

The method of the invention may further comprise administering to the subject one or more factors which enhances differentiation of the haematopoietic precursor cells to a specific haematopoietic lineage cell. The factor which enhances differentiation may be administered simultaneously with the expanded haematopoietic precursor cells, or separately after administration of the expanded haematopoietic precursor cells.

The haematopoietic lineage cell resulting from the differentiation may be, for example, a B-cell, T-cell, dendritic cell, monocyte, neutrophil, macrophage, natural killer cell, granulocyte, erythrocyte, eosinophil, megakaryocyte, platelet, bone marrow, splenic, dermal, or stromal cell.

The factor which enhances differentiation may be, for example, a stem cell factor (SCF), GM-SCF, M-CSF, G-CSF, MGDF, EPO, FLT3-ligand, IL-1, IL-2, IL-3, IL-4, IL-6, IL-7, IL-11, TNFα or thrombopoietin.

Transplantation of the expanded haematopoietic precursor cells may be effected together with the co-cultured MPC or progeny thereof, and/or together with supernatant or one or more soluble factors derived from the co-cultured MPC or progeny thereof.

In one embodiment, administration of haematopoietic precursor cells expanded in accordance with the method of the present invention leads to reduced risk of graft versus host disease when compared to administration of haematopoietic precursor cells that have not been subject to ex vivo expansion. In another embodiment, administration of haematopoietic precursor cells expanded in accordance with the method of the present invention leads to reduced risk of graft versus host disease when compared to administration of haematopoietic precursor cells that have been expanded by methods other than those of the present invention.

It will be appreciated that the method of the invention may be used in the treatment of a range of haematologic disorders.

For example, the method of the invention may be used in the treatment of a disorder of platelet number and/or function such as thrombocytopenia, idiopathic thrombocytopenic purpure (ITP), or a disorder related to viral infection, drug abuse or malignancy.

In another example, the method of the invention may be used in the treatment of a disorder of erythrocyte number and/or function, such as an anaemia. Examples of anaemias that may be treated include aplastic anaemia, autoimmune haemolytic anaemia, blood loss anaemia, Cooley's anaemia, Diamond-Blackfan anaemia, Fanconi anaemia, folate (folic acid) deficiency anaemia, haemolytic anaemia, iron-deficiency anaemia, pernicious anaemia, sickle cell anaemia, thalassaemia or Polycythemia Vera.

In another example, the method of the invention may be used in the treatment of a disorder of lymphocyte number and/or function, such as a disorder caused by a T-cell or B-cell deficiency. Examples of disorders of lymphocyte number and/or function are AIDS, leukemias, lymphomas, Hodgkins lumphoma, chronic infections such as military tuberculosis, viral infections, rheumatoid arthritis, systemic lupus erythematosus, or hereditary disorders such as agammaglobulinemia, DiGeorge anomaly, Wiskott-Aldrich syndrome, or ataxia-telangiectasia.

In another example, method of the invention may be used in the treatment of a disorder of multilineage bone marrow failure, which may be the result of radiotherapy or chemotherapy or malignant replacement. For example, the disorder may be a myelofibrosis, acute myelogenous leukemia (AML), myelodysplastic syndrome (MDS), acute lymphoblastic leukemia (ALL), chromic myelogenous leukemia (CML), chronic lymphocytic leukemia (CLL)), Non-Hodgkin's lymphoma (NHL), Hodgkin's Disease (HD), multiple myeloma (MM), or a secondary malignancy disseminated to bone.

The present invention is applicable to a wide range of animals. For example, the subject may be a mammal such as a human, dog, cat, horse, cow, or sheep. In one embodiment the subject is a human.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

FIG. 1 shows an example of a method for expanding haemopoietic progenitor cells (HPCs) according to the present disclosure. In this example, mesenchymal precursor cells are culture-expanded for 3 days in tissue culture flasks. The culture expanded MPCs are then co-cultured with unmanipulated cord blood cells for seven days, after which a mixture of cytokines is added to the co-culture mix. The mixture is then co-cultured for a further seven days prior to administration of the expanded cord blood cells to the patient.

DETAILED DESCRIPTION OF PREFERRED EMBODIMENT OF THE INVENTION

Figure 1:
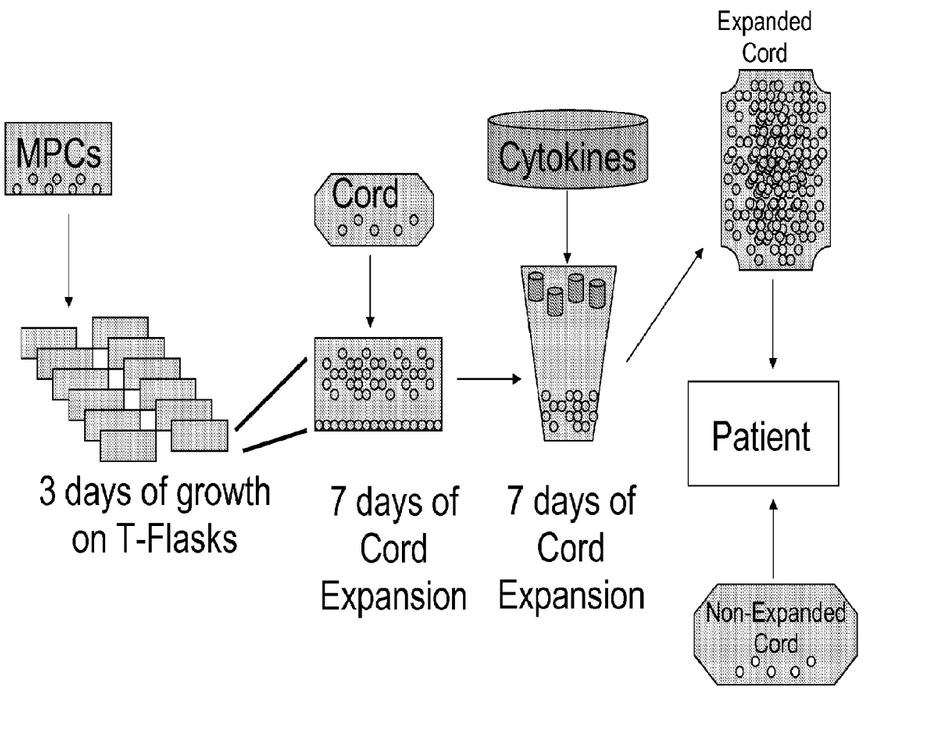

The present invention provides method for the ex vivo expansion of umbilical cord blood derived HPCs by co-culture with mesenchymal precursor cells (MPCs). Such expanded HPCs are useful in the treatment of conditions such as haematopoietic malignancies and in allogeneic cell therapy promoting regeneration of bone marrow.

As used herein, the term "expanding" or "expansion" refers to a process of cellular proliferation. Cells that undergo expansion maintain their cell renewal properties.

The present invention therefore provides a method of transplanting haematopoietic precursor cells into a subject in need thereof, the method comprising:

culturing haematopoietic precursor cells in the presence of a population of cells enriched for STRO-1$^{bright}$ cells or supernatant or progeny derived therefrom, wherein such STRO-1$^{bright}$ cells are mesenchymal precursor cells (MPC) which comprise mesenchymal precursor cells capable of giving rise to colony forming unit-fibroblasts (CFU-F), so as to expand the haematopoietic precursor cells; and administering the expanded haematopoietic precursor cells to a subject.

The term "supernatant" refers to the non-cellular material comprising one or more soluble factors produced following the ex vivo culture of mesenchymal precursor cells, and/or progeny cells thereof, in a suitable medium, preferably a liquid medium. Typically, the supernatant is produced by culturing the cells in the medium under suitable conditions and time, followed by removing the cellular material by a process such as centrifugation. The supernatant may or may not have been subjected to further purification steps before administration. In a preferred embodiment, the supernatant comprises less than $10^5$, more preferably less than $10^4$, more preferably less than $10^3$ and even more preferably no live cells.

The term "one or more soluble factors" refers to molecules, typically proteins, secreted by the MPCs and/or progeny cells thereof, during culture.

In one embodiment of the invention the population of cells enriched for STRO-1$^{bright}$ cells are allogeneic cells. The allogeneic cells may be obtained from an individual with a close HLA match to the subject. An advantage of the present inventions is that the allogenic cells may be produced commercially in bulk for "off-the-shelf" use in ex vivo expansion of haematopoietic precursor cells.

An "off-the shelf" source offers major potential advantages over family member-derived STRO-1$^{bright}$ cells. First, the cells can be made available for immediate use without the need for lengthy processing or the possibility of contamination during culture. The development of master cell banks from young, healthy volunteers offers a way to bypass disease-related decline in stem cell function providing the optimal source of STRO-1$^{bright}$ cells for the cord blood co-cultures. Finally, standardization of selection and isolation procedures provides a very reproducible product.

A further advantage of the method of the invention is that sufficient numbers of STRO-1$^{bright}$ enriched cells used for co-culture with cord blood cells can be obtained considerably faster than with previous methods of de novo generation of MPCs from a bone marrow donor. This allows for patients who are in fragile remission prior to transplant to be treated sooner and thus reduce the likelihood of relapse.

The haematopoietic precursor cells may be derived from any suitable source, one of which is cord blood. It is not necessary to isolate the haematopoietic precursor cells prior to expansion. Accordingly, the method of the invention may involve co-culturing cord blood with a population of cells enriched for STRO-1$^{bright}$ cells or supernatant or progeny derived therefrom. An advantage of this embodiment is that it obviates the need for isolation of CD34$^+$ or CD133$^+$ cells from cord blood prior to expansion, therefore minimising manipulation and loss of haematopoietic precursor cells.

Engraftment can be facilitated by co-administration of a differentiation factor such as a stem cell factor (SCF), GM-SCF, M-CSF, G-CSF, MGDF, EPO, FLT3-ligand, IL-1, IL-2, IL-3, IL-4, IL-6, IL-7, IL-11, TNFα or thrombopoietin. Administration of the differentiation factor may occur at the time of administration of the HPCs and/or at regular intervals after administration of the HPCs.

The haematopoietic lineage cell resulting from the differentiation may be, for example, a B-cell, T-cell, dendritic cell, monocyte, neutrophil, macrophage, natural killer cell, granulocyte, erythrocyte, eosinophil, megakaryocyte, platelet, bone marrow, splenic, dermal, or stromal cell.

Accordingly, the methods of the invention also extend to the optional use of one or more differentiation factors for facilitating haematopoietic reconstitution post infusion of expanded HPCs.

Cells Enriched for STRO-1$^{bright}$ Cells

In one embodiment the method of the present invention involves co-culturing of haematopoietic precursor cells with a population of cells enriched for STRO-1$^{bright}$ cells, wherein such STRO-1$^{bright}$ cells are mesenchymal precursor cells (MPC) which comprise mesenchymal precursor cells capable of giving rise to colony forming unit-fibroblasts (CFU-F).

MPCs are non-hematopoietic progenitor cells that are capable of forming large numbers of multipotential cell colonies. The enrichment of adult MPCs is described in detail in WO 01/04268, the entire contents of which are incorporated by reference. The term "MPCs" according to the present invention is also understood to include the Multipotential Expanded MPC progeny (MEMPs) as defined in WO 2006/032092.

Mesenchymal precursor cells (MPCs) are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into different germ lines such as mesoderm, endoderm and ectoderm. Thus, MPCs are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. Mesenchymal precursor cells are non-hematopoietic progenitor cells which divide to yield daughter cells that are either stem cells or are precursor cells which in time will irreversibly differentiate to yield a phenotypic cell.

In one embodiment, the STRO-1$^+$ cells used in the present invention are also TNAP$^+$, STRO-3$^+$ (TNSAP), VCAM-1$^+$, THY-1$^+$, STRO-2$^+$, CD45$^+$, CD146$^+$, 3G5$^+$ or any combination thereof. For example, the STRO-1$^{bright}$ cells may additionally be one or more of VCAM-1$^+$, THY-1$^+$, STRO-2$^+$, STRO-3$^+$ (TNSAP) and/or CD146$^+$.

In one embodiment, the mesenchymal precursor cells are perivascular mesenchymal precursor cells as defined in WO 2004/85630.

A cell is "positive" for a given marker if it is either a low (lo or dim) or a high (bright, bri) expresser of that marker depending on the degree to which the marker is present on the cell surface, where the terms relate to intensity of fluorescence or other colour used in the colour sorting process of the cells. The distinction of lo (or dim or dull) and bri will be understood in the context of the marker used on a particular cell population being sorted.

The term "bright", when used herein, refers to a marker on a cell surface that generates a relatively high signal when detectably labelled. Whilst not wishing to be limited by theory, it is proposed that "bright" cells express more of the target marker antigens. For instance, STRO-1$^{bri}$ cells produce a greater fluorescent signal, when labelled with a FITC-conjugated STRO-1 antibody as determined by FACS analysis, than non-bright cells (STRO-1$^{dull/dim}$). In another example, STRO-1$^{bright}$ cells have 2 log magnitude higher expression of STRO-1 surface expression relative to an isotype matched negative control. By comparison, STRO-1$^{dim}$ and/or STRO-1$^{intermediate}$ cells have less than 2 log magnitude higher expression of STRO-1 surface expression, typically about 1 log or less higher expression over the isotype matched negative control.

The population of cells used in the present invention is preferably enriched for STRO-1$^+$ cells relative to STRO-1$^{dim}$ and/or STRO-1$^{intermediate}$ cells.

When used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

It is preferred that a significant proportion of the MPCs are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another embodiment, the MPCs are not capable of giving rise, upon culturing, to hematopoietic cells.

The present invention also relates to use of supernatant or soluble factors obtained from MPCs and/or progeny cells thereof (the latter also being referred to as expanded cells) which are produced from the in vitro culture of freshly isolated MPCs. Expanded cells of the invention may a have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Preferably, the medium used in the co-culture methods of the present invention is a liquid medium.

Preferably, the culture medium is supplemented with one or more growth factors or cytokines which support the expansion of HPCs. Preferably, the cytokines are early acting cytokines, such as, but not limited to recombinant metHu stem cell factor (SCF), flt-3 ligand (FLT3), IL-1, IL-2, IL-3, IL-6, IL-10, IL-12, tumor necrosis factor-α and thrombopoietin.

Late acting cytokines can also be used. These include for example, granulocyte colony stimulating factor (G-CSF), granulocyte/macrophage colony stimulating factor (GM-CSF), erythropoietin (EPO), LIE and macrophage growth factor (M-CSF).

Multipotential Expanded MPC Progeny (MEMPs) are defined in WO 2006/032092. Methods for preparing enriched populations of MPC from which progeny may be derived are described in WO 01/04268 and WO 2004/085630. In an in vitro context MPCs will rarely be present as an absolutely pure preparation and will generally be present with other cells that are tissue specific committed cells (TSCCs). WO 01/04268 refers to harvesting such cells from bone marrow at purity levels up to about 90%. The population comprising MPC from which progeny are derived may be directly harvested from a tissue source, obtained from a master cell bank, or alternatively it may be a population that has already been expanded ex vivo.

For example, the progeny may be obtained from a harvested, unexpanded, population of substantially purified MPC, comprising at least about 0.1, 1, 5, 10, 20, 30, 40, 50, 60, 70, 80 or 95% of total cells of the population in which they are present. This level may be achieved, for example, by selecting for cells that are positive for at least one marker selected from the group consisting of TNAP, STRO-1$^{bright}$, 3G5$^+$, VCAM-1, THY-1, CD146 and STRO-2.

The MPC starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

MEMPs can be distinguished from freshly harvested MPCs in that they are positive for the marker STRO-1$^{bri}$ and negative for the marker alkaline phosphatase (ALP). In a preferred embodiment of the present invention, at least 15%, 20%, 30%, 40%, 50%, 60%, 70%, 80%, 90% or 95% of the cells have the phenotype STRO-1$^{bri}$, ALP$^-$. In a further preferred embodiment, the MEMPs are positive for one or more of the markers Ki67, CD44 and/or CD49c/CD29, VLA-3, α1β1. In yet a further preferred embodiment, the MEMPs do not exhibit TERT activity and/or are negative for the marker CD18.

Once a suitable MPC population has been obtained, it may be cultured or expanded by any suitable means to obtain MEMPs.

In a preferred embodiment of the invention, the MPCs are obtained from a master cell bank derived from MPCs enriched from the bone marrow of young healthy volunteers. The use of MPCs derived from such a source is particularly advantageous for subjects who do not have an appropriate family member available who can serve as the MPC donor. Furthermore, other subjects, in particular those with acute leukemia are in fragile remissions prior to transplant and at high risk of relapsing during the lengthy time it takes to generate MPCs and then perform co-cultures. An "off-the-shelf" source offers major potential advantages over the family member-derived MPCs as the cells are available for immediate use without the need for lengthy processing or the possibility of contamination during culture. The development of master cell banks offers a way to bypass disease-related decline in stem cell function providing the optimal source of MPCs for the cord blood co-cultures.

The Applicant has developed an off-the-shelf ex vivo expanded allogeneic MPC product for the treatment of chronic ischemic cardiovascular disease, referred to as "Mesenchymal Precursor Cell" or Revascor™. Bone marrow cells are harvested from the posterior iliac crest of healthy human donors. The mononuclear cells are immunoselected for stromal enrichment using the STRO-3 (TNSAP) monoclonal antibody (Simmons P J et al., (1991)), subsequently expanded, and cryopreserved to produce a cell bank. The expansion of immunoselected bone marrow mononuclear cells concentrated for mesenchymal precursors yields a product with defined purity, expression of mesenchymal precursor specific markers, and potent biological activity. Furthermore, work by the present Applicant and others confirms the immunological tolerance of their allogeneic MPCs in a variety of preclinical and clinical allogeneic settings.

Since the Applicant's commercially available source of MPCs do not express HLA-II (DR), they are therefore non-immunogenic and provide an ideal MPC source for use in the present invention.

Cord Blood

Exsanguination of the umbilical cord blood can be achieved by, for example, but not by way of limitation, draining, gravity induced efflux, massaging, squeezing, pumping, etc. In a preferred embodiment, exsanguination of the umbilical cord is achieved by use of a syringe that may or may not include an anticoagulant.

Cord blood used in the methods of the present invention can be obtained through a commercial source e.g. LifeBank USA (Cedar Knolls, N.J.), ViaCord (Boston Mass.), Cord Blood Registry (San Bruno, Calif.) and Cryocell (Clearwater, Fla.).

Methods for harvesting cord blood cells are known in the art. Examples of such methods are also described in the patent literature including, for example, U.S. Pat. No. 5,916,202 entitled "Umbilical cord blood collection" and U.S. Pat. No. 7,147,626 entitled "Cord blood and placenta collection kit".

In one embodiment, the cord blood is matched with the subject at 4, 5 or 6/6 HLA class I (serological) and II (molecular) antigens. In another embodiment, at least two cord blood units are used per subject. The cord blood units may be cryogenically frozen prior to use or used straight away when harvested from the umbilical cord.

Prior to culture, the cord blood cells may be enriched for $CD34^+$ progenitor cells, or they may be enriched for progenitor cells based on expression of the marker CD133.

In one embodiment, the cord blood cells are unmanipulated prior to their addition to the MPCs.

In another embodiment, the cord blood cells are added to confluent monolayers of pre-established MPCs or MEMPs.

In another embodiment, the cord blood units are co-cultured for around 14 days in a suitable ex vivo expansion medium. The expansion medium used for the co-culture may comprise fetal bovine serum, glutamine and suitable growth factors.

In one embodiment of the invention, the number of expanded HPCs used to treat a subject is in the range of from $\geq 1.0 \times 10^7$ TNC/kg to $\geq 4.0 \times 10^7$ TNC/kg.

Co-Culture Conditions

In one embodiment of the present invention, haematopoietic precursor cells, or unmanipulated cord blood cells, are added to an established adherent MPC cell culture. The MPCs may be cultured to confluence, replated and re-cultured to provide a feeder layer to which is added the cord blood cells for co-culturing.

One advantage of embodiments of present invention is that sufficient numbers of confluent adherent allogeneic MPCs for co-culture can be obtained within about four days after initiating MPCs from a single cryopreserved vial (containing $\geq 1.5 \times 107$ cells/ml at cryopreservation). Sufficient numbers of MPCs according to the invention is where enough cells are present to reach >70% confluency in $12 \times T$-150 $cm^2$ tissue culture flasks (per subject). This is considerably faster than prior art methods of generating MPCs de novo from a bone marrow donor, which typically takes about four weeks.

In one embodiment of the invention, cord blood cells are co-cultured with MPCs in an ex vivo expansion medium comprising fetal bovine serum, glutamine, G-CSF, SCF, FLT3-ligand and thrombopoietin.

The cells may be co-cultured for a period of about 14 days.

Administration of HPCs to the Subject

According to the methods of the present invention, the ex vivo expanded HPCs (which may or may not further include the co-cultured MPCs or MEMPs) are implanted into a subject having a haematological malignancy. In a preferred embodiment, the subject is a human.

Modes of administration of the cells include, but are not limited to, systemic intravenous injection. The cell preparation can be administered by any convenient route, for example by infusion or bolus injection and can be administered together with other biologically active agents.

In some embodiments, regimes for reducing implant rejection and/or graft vs. host disease of the HPCs may be practiced, particularly in circumstances where the allogeneic MPCs are also provided to the subject. Such regimes are known in the art. See, for example Slavin S et al., J Clin Immunol. 2002 22:64. Typical GVHD prophylaxis agents include antithymocyte globulin (ATG), mycophenalate mofetil (MMF), and tacrolimus.

It will be appreciated that the HPCs can be provided along with the culture medium supernatant or one or more factors derived from co-cultured MPCs isolated from the culture medium, and administered in a pharmaceutically acceptable carrier. Hence, cell populations of the invention can be administered in a pharmaceutically acceptable carrier or diluent, such a sterile saline and aqueous buffer solutions. The use of such carriers and diluents in well known in the art.

In one example, the expanded HPCs are provided alone with MPCs or MEMPs of the co-culture. In another example, the HPCs are provided without MPCs or MEMPs. Methods for the separation of mesenchymal cells and haemopoietic cells are well known in the art, and include, but are limited to, affinity separation (according to markers present on mesenchymal cells and haemopoietic cells) by chromatography, batch separation and/or flow cytometry (FACS).

MPCs, MEMPs or supernatant derived therefrom can be administered prior to, simultaneously with or after administration of the HPCs.

Haematopoietic Reconstitution

In one embodiment of the invention, haematopoietic reconstitution occurs in the subject following administration of the expanded haematopoietic precursor cells. For example, haematopoietic reconstitution may occur in the subject within 30 days, more preferably within 25 days, more preferably within 20 days, more preferably within 15 day and more preferably within 10 days of administration of the expanded haematopoietic precursor cells.

Haematopoietic reconstitution may determined by any one of a number of suitable measurements. For example, haematopoietic reconstitution is taken to have occurred once any one or more of the following have occurred: neutrophil engraftment, platelet engraftment, lymphoid engraftment, white blood cell engraftment, red blood cell engraftment, erythroid engraftment and/or megakaryocyte engraftment.

Neutrophil Engraftment

Neutrophil engraftment is defined as sustained absolute neutrophil count (ANC) which is greater than or equal to $0.5 \times 10^9$/L for 3 consecutive days.

Platelet Engraftment

Platelet engraftment is defined as the first of three consecutive days when the unsupported platelet count was greater than $50 \times 10^9$/L.

White Blood Cell Engraftment

White blood cell engraftment is defined as the first of three consecutive days an absolute polymorphonuclear cells (PMN) were greater than $50 \times 10^9$/L.

Red Blood Cells (RBC) Engraftment

Red blood cells (RBC) engraftment may be recorded using measurement of HbF and looking at F cells on blood films.

For example, red blood cell engraftment may have occurred when the HbF is about 3.6% and the F cells are about 7-8%.

The invention will now be described in more detail with reference to the following non-limiting examples.

EXAMPLES

Example 1

Comparison of "Off-the Shelf" Allogeneic MPCs with Autologous MSCs

Cord blood (CB) co-cultured with MSCs generated de novo from bone marrow was compared with cord blood co-cultured with the Applicants "off-the-shelf" MPCs (Robinson et al., 2007).

MSCs are generated de novo from bone marrow as follows. Approximately 80-100 ml of marrow is aspirated into sterile heparin-containing syringes and taken to the MDACC Cell Therapy Laboratory for MSC generation. The bone marrow mononuclear cells are isolated using ficoll-hypaque and placed into two T175 flask with 50 ml per flask of MSC expansion medium which includes alpha modified MEM ($\alpha$MEM) containing gentamycin, glutamine (2 mM) and 20% (v/v) fetal bovine serum (FBS) (Hyclone).

The cells are cultured for 2-3 days in 37° C., 5% $CO_2$ at which time the non-adherent cells will be removed; the remaining adherent cells will be continually cultured until the cell confluence reaches 70% or higher (7-10 days), and then the cells will be trypsinized and replaced in six T175 flasks with MSC expansion medium (50 ml of medium per flask). The cells are cultured in 37° C., 5% $CO_2$ for an additional week. On day 14 (+/−5 days) the six flasks of MSCs with 70% or higher confluence are split again into 12 flasks and cultured in MSC expansion medium for a third week as above. The MSC monolayers, which will be >70% confluent at this time, are then ready for the CB expansion which should be initiated on chemotherapy day −14. If the MSCs are ready before day −14, the MSC monolayers are maintained by a weekly medium change with MSC culture medium until ready for use.

Two frozen cord blood units were thawed, washed and co-cultured with adherent monolayers from each source (MSCs or MPCs) for 14 days using the presence of growth factors SCF, FLT3-ligand, G-CSF and TPO). As shown in Table 1, allogeneic MPCs are better at expanding cord blood CD34 progenitor cells than the allogeneic MSCs.

TABLE 1

| Study | "N" | Avg. TNC fold increase | Avg. CD34+ fold increase |
|---|---|---|---|
| Allogeneic MSC cord expansion | 6 | 13 | 14 |
| Pre-clinical Allogeneic MPC cord expansion | 5 | 12.6 | 29 |
| Clinical Allogeneic MPC cord expansion | 9(TNCs); 11(CD34+) | 16 | 39 |

Example 2

Time to Generation of Sufficient Numbers of "Off the Shelf" MPCs for Cord Blood Co-Culture One vial containing frozen human mesenchymal precursor cells (Lot No. 25126787, >1.5×10$^7$ cells/ml) was thawed and 2.03×10$^6$ cells recovered into 360 mls of alphaMEM medium supplemented with antibiotics (penicillin and streptomycin), glutamine and 10% (v/v) fetal bovine serum (FBS). The cell suspension was then distributed between 12×T-150 cm$^2$ tissue culture flasks (approximately 1.7×10$^6$ cells per T-150 cm$^2$ tissue culture flask). Cultures were monitored using inverted, phase contrast microscopy. Four to five days after initiation of the culture, the MPCs were >70% confluent and could be used for cord blood mononuclear cells (MNC) co-culture expansion. Accordingly, it is likely that the cultured MPCs would be sufficiently confluent by four days after initiation of the culture. This indicates that a single vial of off-the-shelf MPCs are sufficient to generate sufficient numbers of cells for cord blood co-culture after 3-5 days in culture. This represents a significant reduction from the approximately four weeks of expansion culture required to achieve sufficient numbers of confluent MPCs for co-culture from a bone marrow aspirate.

Example 3

Cord Blood Transplantation Protocols 3.1 Double Cord Blood Transplants

In an attempt to increase the number of CB cells infused following high-dose or nonmyeloablative therapy, investigators have combined two units of differing HLA types and infused them as allogeneic hematopoietic support. These investigations support the principle that transplantation of two immunologically distinct CB units is safe in terms of crossed immunological rejection. Graft failure was not observed, but the majority of patients did engraft with only a single CB unit. In the current trial we will use two CB units, one of which will be expanded ex vivo in attempt to reduce the time to engraftment in CB transplant recipients below the 20-30 days typically reported in this setting.

3.2 Growth Factors for Ex-Vivo Expansion

The CB cells will be cultured with very low concentrations of the growth factors described in this section (nanogram concentrations as opposed to the microgram concentrations used systemically). Additionally, the expanded cells will be washed extensively prior to infusion into the patient. Thus, it is unlikely that they will produce any systemic side effects.

Suitable growth factors are described below.

1. Filgrastim [Granulocyte Colony Stimulating Factor (G-CSF)]

Therapeutic classification: Recombinant Growth Factor

Mechanism of action: G-CSF is a human granulocyte-stimulating factor that acts on hematopoietic cells to stimulate proliferation, differentiation, and some end-cell functional activity.

Storage and stability: G-CSF should be stored at 2-8° C. Prior to injection, Filgrastim may be allowed to reach room temperature, however, any vials left at room temperature for greater than 24 hours should be discarded. Vials should not be shaken. Vials should be inspected for sedimentation or discoloration prior to administration. If sedimentation or discoloration is observed, the vials should not be used.

Route of administration: SC Injection-IV Infusion

Incompatibility: No definite incompatibilities are known. However, drugs that may potentiate the release of neutrophils should be used with caution.

Availability: Commercially available in single-dose, preservative-free vials containing 300 mcg (1 ml vial) and 48 0mcg (1.6 ml vial) of Filgrastim.

Side effects: Mild to moderate bone pain is possible in patients receiving myelosuppressive therapy. General skin rash, alopecia, fevers, thrombocytopenia, osteoporosis, nausea, vomiting, diarrhea, mucositis, anorexia, inflammation of the blood vessels, and/or cardiac dysrhythmia can occur. Splenomegaly may result at high doses of Filgrastim.

2. Recombinant-metHuStem Cell Factor (SCF).

Therapeutic classification: Recombinant Growth Factor

Mechanism of action: SCF is a human granulocyte-stimulating factor that acts on hematopoietic cells to stimulate proliferation, differentiation, and some end-cell functional activity.

Pharmaceutical data: Recombinant methionyl human stem cell factor (r-metHuSCF) is a recombinant human protein produced in *E. coli* by recombinant DNA technology. The 165-amino acid non-glycosylated protein contains two intramolecular disulfide bonds, exists as a non-covalently associated dimer with a molecular weight of 36,000, and differs from the natural protein by the presence of a methionine moiety at the N-terminus (residue number [−1]) resulting from the expression in and in the fact that the recombinant protein is not glycosylated. Cells expressing r-metHuSCF are grown in culture under defined and controlled conditions. The cells are harvested yielding a paste from which the r-metHuSCF is extracted and purified via a series of proprietary processing and chromatographic steps. The resulting purified r-metHuSCF is formulated in an aqueous buffer before undergoing sterile filtration and filling. Criteria for release of r-metHuSCF for use in the clinic are stringent. These include passing the USP rabbit pyrogen test, the limulus amebocyte assay, a sterility test, and the general safety test (Code of Federal Regulations, Title 21, Section 610.11). The nucleic acid content is no greater than 1.7 pg/mg protein. The final product is a clear, colorless, sterile protein solution free of particulates; r-metHuSCF is not less than 95% pure. Biologic activity of purified preparations is assessed via radioreceptor binding and proliferation assays.

Storage and stability: Recombinant-metHuSCF must be stored at 2-8° C. Stability of r-metHuSCF at concentrations of 1.5 mg/ml has been demonstrated for 12 months when stored under these conditions. Stability testing is ongoing. Exposure of the material to excessive temperatures above or below this range is to be avoided. Do not allow r-metHuSCF to freeze, and do not use if contents freeze in transit or in storage.

SIDE EFFECTS: Not known but injection site complication such as urticaria and erythema 3. Thrombopoietin (TPO)

Therapeutic classification: Recombinant Growth Factor

MECHANISM OF ACTION: TPO is a human granulocyte-stimulating factor that acts on hematopoietic cells and in particular megarkyocyte progenitors to stimulate proliferation, differentiation, and some end-cell functional activity.

Storage and stability: TPO should be stored at 2-8° C. Vials should not be shaken. Vials should be inspected for sedimentation or discoloration prior to administration. If sedimentation or discoloration is observed, the vials should not be used.

Known side effects: thrombocytosis, deep-vein thrombosis, pulmonary embolism, thrombophlebitis.

4. FLT3-Ligand (FLT3)

Therapeutic classification: Recombinant Growth Factor

Mechanism of action: FLT3 s a human granulocyte-stimulating factor that acts on hematopoietic cells.

Storage and stability: FLT3 should be stored at 2-8° C. Vials should be inspected for sedimentation or discoloration prior to administration. If sedimentation or discoloration is observed, the vials should not be used.

Known side effects: thrombocytosis, deep-vein thrombosis, pulmonary embolism, thrombophlebitis.

3.3 Administration of Off-the-Shelf MPCs.

Angioblast Revascor™ MPCs are used for the CB co-cultures. A single frozen vial of Angioblast Revascor™ MPC will supply sufficient cells to seed three (3) to four (4) T-300 cm2 culture flasks. After recovery from thawing and after a period of 2-3 days of culture in αMEM medium supplemented with ten (10) percent fetal bovine serum (MPC culture medium), adherent cells will be collected by trypsinization and the whole transferred into twelve (12) T-150 cm2 culture flasks. Cells will be cultured in MPC culture medium in the twelve (12) T-150 cm2 culture flasks for an additional five (5) to six (6) days until growth sufficient to achieve greater than 70% confluence over the available culture surface is achieved. At this point the T-150 cm2 culture flasks will be released for use in the cord blood co-culture expansion protocol. Culture flasks generated in this manner can be maintained at >70% confluence until required by a weekly medium change. Ten (10) of the twelve (12) T-150 cm2 culture flask generated and containing MPC at >70% confluence will receive ten (10) percent of a thawed, washed cord blood unit. Co-culture will be performed in culture medium supplemented with fetal bovine serum and containing 100 ng/ml each of SCF, FLT3-L, TPO and G-CSF as described above for the family member-derived MSCs.

Patients will be admitted to the hospital on day −9 for hydration and receive the designated preparative regimen on days −8 through −2. On day 0, the unmanipulated CB unit will be infused followed by the expanded CB unit. On day 0 (culture day 14), the cells from both cultures will be harvested and washed for infusion.

Example 4

Clinical Trial Results

Fourteen patients were transplanted with MPC induced expanded cord blood in an ongoing trial. The average age of the patient was 40 years. Current results of the transplants are shown in Table 2 below.

The median time to neutrophil engraftment was 17 days (compared to historic controls of 34 days). The median time to platelet engraftment was 38 days (compared to historic controls of 128 days). No patients had Grade III/IV GVHD (compared to historic controls of 40%).

Table 3 shows that current MPC induced expanded cord blood transplantation results are superior to alternative cord blood expansion strategies.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

TABLE 2

| Patient | Date of transplant | Time to neutrophil engraftment | Platelet engraftment | GVHD |
|---|---|---|---|---|
| 1 | Dec. 9, 2008 | Day 12 (Dec. 21, 2008) | Day 57 (Feb. 4, 2009) | BX positive GVDH GI Duodenum |
| 2 | Feb. 10, 2009 | Day 22 (Mar. 4, 2009) | Day 18 (Feb. 28, 2009) | Negative |
| 3 | Feb. 13, 2009 | Day 15 (Feb. 28, 2009) | Day 37 (Mar. 22, 2009) | Negative |
| 4 | May 12, 2009 | Day 13 (May 25, 2009) | Day 29 (Jun. 10, 2009) | Negative |
| 5 | May 19, 2009 | Day 19 (Jun. 7, 2009) | Day 45 (Jul. 3, 2009) | BX positive GVDH GI Duodenum, stomach, colorectal |
| 6 | Jun. 4, 2009 | Day 25 (Jun. 29, 2009) | Day 39 (Jul. 13, 2009) | Negative |
| 7 | Jun. 15, 2009 | N/A | N/A | Negative |
| 8 | Jun. 23, 2009 | Day 24 (Jul. 17, 2009) | N/A | |
| 9 | Off study | Off study | Off study | Off study |
| 10 | Jul. 6, 2009 | Day 9 (Jul. 15, 2009) | N/A | |
| 11 | Aug. 3, 2009 | N/A | N/A | |
| 12 | Jul. 21, 2009 | N/A | N/A | |
| 13 | Jul. 23, 2009 | N/A | N/A | |
| 14 | Aug. 7, 2009 | N/A | N/A | |

TABLE 3

| Product | "N" | TNC Expansion fold | CD34 Expansion Fold | Median time to neutrophil engraftment | Median time to platelet engraftment | Rate of GVHD as Grade 2 or Greater 2 |
|---|---|---|---|---|---|---|
| Angioblast Allogeneic MPC | 14 | 16 | 39 | 17 | 38 | 0% |
| *Aastrom Biosciences Replicall ™ | 28 | 2.4 | 0.5 | 22 | 71 | 36% |
| **Viacell Selected Amplification ™ | 10 | 219 | | 24 | 54 | 40% |
| ***Gamida StemEx ™ | 10 | | 6 | 30 | 48 | 44% G2, 50% chronic GVHD post day 100 |
| ****Historic Control (New York Blood Center) | 97 adults (560 patients including pediatric) | N/A | N/A | 28 | 90 | 46% (Adults and Pediatric combined rate) |

*Jaroscak et al., 2003
**Chan et al., 2006
***de Lima et al., 2008
****Rubinstein et al., 1998

REFERENCES

Barker, J. N., S. M. Davies, T. DeFor, N. K. Ramsay, D. J. Weisdorf, and J. E. Wagner, Survival after transplantation of unrelated donor umbilical cord blood is comparable to that of human leukocyte antigen-matched unrelated donor bone marrow: results of a matched-pair analysis. Blood, 2001. 97(10): p. 2957-61.

Chan, S. L et al., Enhanced in vivo homing of uncultured and selectively amplified cord blood CD34+ cells by co-transplantation with cord-blood derived unrestricted somatic stem cells. Stem Cells, 2006. 25:529-536.

De Lima, M. et al. Transplanatation of ex vivo expanded cord blood cells using the copper chelator tetraethylenepentamine: a phase I/II clinical trial. Bone Marrow Transplantation, 2008., 1-8.

Gluckman, E., V. Rocha, A. Boyer-Chammard, F. Locatelli, W. Arcese, R. Pasquini, J. Ortega, G. Souillet, E. Ferreira, J. P. Laporte, M. Fernandez, and C. Chastang, Outcome of cord-blood transplantation from related and unrelated donors. Eurocord Transplant Group and the European Blood and Marrow Transplantation Group. N. Engl. J. Med., 1997. 337(6): p. 373-81.

Jaroscak. J. et al., Augmentation of umbilical cord blood transplantation with ex-vivo expanded UCB cells: results of phase I trial using Aastrom Replicell system. Blood, 2003. 101:5061-5067.

Kernan, N. A., G. Bartsch, R. C. Ash, P. G. Beatty, R. Champlin, A. Filipovich, J. Gajewski, J. A. Hansen, J. Henslee-Downey, and J. McCullough, Analysis of 462 transplantations from unrelated donors facilitated by the National Marrow Donor Program. N. Engl. J. Med., 1993. 328(9): p. 593-602.

Kurtzberg, J., M. Laughlin, M. L. Graham, C. Smith, J. F. Olson, E. C. Halperin, G. Ciocci, C. Carrier, C. E. Stevens, and P. Rubinstein, Placental blood as a source of hematopoietic stem cells for transplantation into unrelated recipients. N. Engl. J. Med., 1996. 335(3): p. 157-66.

Laughlin, M. J., J. Barker, B. Bambach, O. N. Koc, D. A. Rizzieri, J. E. Wagner, S. L. Gerson, H. M. Lazarus, M. Cairo, C. E. Stevens, P. Rubinstein, and J. Kurtzberg, Hematopoietic engraftment and survival in adult recipients of umbilical-cord blood from unrelated donors. N. Engl J Med., 2001. 344(24): p. 1815-22.

Rizzieri, D. A., G. D. Long, J. J. Vredenburgh, C. Gasparetto, A. Morris, D. Niedzwiecki, M. Lassiter, J. Loftis, P. Davis, C. McDonald, T. Stenzel, B. Waters-Pick, J. Kurtzberg, and N. J. Chao, Durable Engraftment of Mismatched Unrelated Cord Blood Following a Non-Myeloablative Prepative Regimen for Adults. Blood, 2001. 98(11 (1)): p. 185a.

Robinson, S. N. et al., Efficacy of "Off-the-Shelf" commercially available, third-party mesenchymal stem cells (MSC) in ex vivo cord blood (CB) co-culture expansion. Blood (ASH Annual Meeting Abstracts) 2007 110: Abstract 4106.

Rubinstein, P., C. Carrier, A. Scaradavou, J. Kurtzberg, J. Adamson, A. R. Migliaccio, R. L. Berkowitz, M. Cabbad, N. L. Dobrila, P. E. Taylor, R. E. Rosenfield, and C. E. Stevens, Outcomes among 562 recipients of placental-blood transplants from unrelated donors. N. Engl. J. Med., 1998. 339(22): p. 1565-77.

The invention claimed is:

1. A method of reducing the risk of developing graft versus host disease in a subject in need thereof, the method comprising:
   culturing haematopoietic precursor cells in the presence of a population of cells enriched for STRO-1$^{bright}$ cells or supernatant or progeny derived therefrom, wherein such STRO-1$^{bright}$ cells are mesenchymal precursor cells (MPC) which comprise mesenchymal precursor cells capable of giving rise to colony forming unit-fibroblasts (CFU-F), so as to expand the haematopoietic precursor cells; and
   administering the expanded haematopoietic precursor cells in combination with STRO-1$^{bright}$ cells or progeny thereof to a subject,
   wherein the risk of developing host versus graft disease by the subject is reduced when compared to administration of haematopoietic precursor cells that have not been cultured in the presence of a population of cells enriched for STRO-1$^{bright}$ cells or progeny thereof.

2. The method of claim 1, wherein the population of cells enriched for STRO-1$^{bright}$ cells are allogeneic cells.

3. The method of claim 1 wherein haematopoietic reconstitution occurs in the subject within 10 to 30 days of administration of the expanded haematopoietic precursor cells.

4. The method of claim 3 wherein haematopoietic reconstitution occurs in the absence of an adverse immune response.

5. The method of claim 3 wherein haematopoietic reconstitution is determined by neutrophil engraftment, platelet engraftment, lymphoid engraftment, erythroid engraftment and/or megakaryocyte engraftment.

6. The method of claim 1 which further comprises administering to the subject a factor which enhances differentiation of the haematopoietic precursor cells to a specific haematopoietic lineage cell.

7. The method of claim 6 wherein the haematopoietic lineage cell is a B-cell, T-cell, dendritic cell, monocyte, neutrophil, macrophage, natural killer cell, granulocyte, erythrocyte, eosinophil, megakaryocyte, platelet, bone marrow, splenic, dermal, or stromal cell.

8. The method of claim 6 wherein the factor which enhances differentiation is stem cell factor (SCF), GM-SCF, M-CSF, G-CSF, MGDF, EPO, FLT3-ligand, IL-I, IL-2, IL-3, IL-4, IL-6, IL-7, IL-I 1, TNFα or thrombopoietin.

9. The method of claim 1 wherein the subject has a haematologic disorder.

10. The method of claim 9 wherein the haematologic disorder is thrombocytopenia, idiopathic thrombocytopenic purpure (ITP), or a disorder related to viral infection, drug abuse or malignancy.

11. The method of claim 9 wherein the haematologic disorder is a disorder of erythrocyte number and/or function.

12. The method of claim 11 wherein the haematologic disorder is an anaemia.

13. The method of claim 12 wherein the anaemia is aplastic anaemia, autoimmune haemolytic anaemia, blood loss anaemia, Cooley's anaemia, Diamond-Blackfan anaemia, Fanconi anaemia, folate (folic acid) deficiency anaemia, haemolytic anaemia, iron-deficiency anaemia, pernicious anaemia, sickle cell anaemia, thalassaemia or Polycythemia Vera.

14. The method of claim 9 wherein the haematologic disorder is a disorder of lymphocyte number and/or function.

15. The method of claim 14 wherein the disorder is due to a T-cell or B-cell deficiency.

16. The method of claim 14 wherein the disorder is AIDS, a leukemia, a lymphoma, Hodgkins lumphoma, a chronic infection such as military tuberculosis, a viral infection, rheumatoid arthritis, systemic lupus erythematosus, or a hereditary disorder such as agammaglobulinemia, DiGeorge anomaly, Wiskott-Aldrich syndrome, or ataxia-telangiectasia.

17. The method of claim 9 wherein the haematologic disorder is a result of radiotherapy or chemotherapy.

18. The method of claim 9 wherein the haematologic disorder is a result of malignant replacement.

19. The method of claim 9 wherein the haematologic disorder is myelofibrosis, acute myelogenous leukemia (AML), myelodysplastic syndrome (MDS), acute lymphoblastic leukemia (ALL), chromic myelogenous leukemia (CML), chronic lymphocytic leukemia (CLL)), Non-Hodgkin's lymphoma (NHL), Hodgkin's Disease (HD), multiple myeloma, or a secondary malignancy disseminated to bone.

* * * * *